United States Patent [19]

Kawakami et al.

[11] Patent Number: 4,659,786

[45] Date of Patent: Apr. 21, 1987

[54] LOW MODULUS THERMOPLASTIC ELASTOMERIC POLYESTER-POLYSILOXANE BLOCK COPOLYMERS

[75] Inventors: Michio Kawakami, Sendai; Yoshima Araki, Izumi; Kenkichi Murakami; Hidetoshi Oikawa, both of Sendai; Michio Nakanishi, Niiza; Makoto Hosotani, Sendai, all of Japan

[73] Assignee: Tohoku University, Sendai, Japan

[21] Appl. No.: 740,259

[22] Filed: Jun. 3, 1985

[30] Foreign Application Priority Data

Sep. 11, 1984 [JP] Japan ................................. 59-188911

[51] Int. Cl.⁴ ........................ C08G 63/08; C08G 81/00
[52] U.S. Cl. .................................. 525/415; 525/446; 525/474

[58] Field of Search ......................... 525/415, 474, 446

[56] References Cited

U.S. PATENT DOCUMENTS 4,202,807 5/1980 Moretto et al. ......................... 528/28
4,539,379 9/1985 Hallgren ............................... 525/474

Primary Examiner—Wilbert J. Briggs, Sr.
Attorney, Agent, or Firm—Fleit, Jacobson, Cohn & Price

[57] ABSTRACT

Polyester-polysiloxane block copolymers for dental uses are disclosed as low modulus thermoplastic elastomers. The copolymers comprise polycaprolactone residues and poly(dimethylsiloxane) α,ω-diol residues which are linked by ether bonds. The compounds exhibit the property of plasticity by heating and the property of original rubber elasticity by cooling again to room temperature.

7 Claims, 4 Drawing Figures

1: Poly (Dimethylsiloxane)
2: Polycaprolactone
3: Compound of this Invention

LOW MODULUS THERMOPLASTIC ELASTOMERIC POLYESTER-POLYSILOXANE BLOCK COPOLYMERS

FIELD OF THE INVENTION

The present invention relates to low modulus thermoplastic elastomers which are used as dental impression materials, mold materials for general uses and various sealing materials.

BACKGROUND OF THE INVENTION

Silicone, polysulfide and polyether synthetic rubbers vulcanizable at room temperature are used as dental impression materials, mold materials for general uses and sealing materials. As any of these synthetic rubbers, however, have relatively high production costs and are obtained by complex reactions, there are problems of operation and quality control. Further, since these synthetic rubbers are obtained by use of irreversible reactions, if once these are used, these can not be reused and must be wasted. Namely, there are problems in the aspect of costs and effective uses of resources.

As materials for solving these problems, the so-called thermoplastic elastomers have been noticed. The thermoplastic elastomers have a general term of high-molecular weight materials which show rubber elasticity at room temperature and easily give plasticity and moldability at high temperature. In the molecular structures, the elastomers are copolymers in which hard segments and soft segments combine. Thermoplastic elastomers by combinations of various hard segments and soft segments including polystyrene-polybutadiene copolymer have already existed as known compounds. However, any of them has relatively high modulus or high softening temperature which renders them unsuited to use as mold materials for general uses and sealing materials including dental impression materials.

Thermoplastic elastomers which are suitable for uses of dental impression materials, mold materials for general uses and sealing materials should have good rubber elasticity at room temperature, furthermore softening temperature of about 50° C. and Young's modulus of about 2 MPa and under.

SUMMARY OF THE INVENTION

Accordingly, for developing new materials which are repeatedly usable in the above application and have good rubber elasticity, the present invention provides new compounds satisfying the following conditions;

(a) The compounds are teleblock or multiblock copolymers which consist of hard segments and soft segments.

(b) The hard segments have crystallizability and sharp softening temperature of about 50° C.

(c) The soft segments have excellent properties as rubber polymers, which are small cohesive energy and great fusion entropy.

(d) The Young's modulus of the block copolymers is about 2 MPa and under and viscosity at the time of fusion is $10^3$ Pa.S and under.

In the present invention, the compounds satisfying the above conditions are polyester-polysiloxane block copolymers represented by the general formula

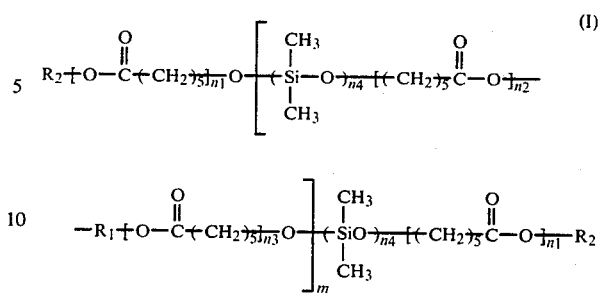

wherein $R_1$ is a polymerization initiator residue of ε-caprolactone, the polymerization initiator being a compound having two or more active hydrogens and producing two or more terminal OH, $R_2$ are polymerization initiator residues of ε-caprolactone, the polymerization initiator being a compound having an active hydrogen and producing a terminal OH, and $n_1$, $n_2$, $n_3$, $n_4$ and $m$ are numbers of structural units, respectively.

DETAILED DESCRIPTION OF THE INVENTION

Namely, polyester-polysiloxane block copolymers of the present invention are new thermoplastic elastomers comprising of polycaprolactone residues (A) which have an hydroxide residue at the one terminal group, polycaprolactone residues (B) which have hydroxide residues at both the terminal groups and poly(dimethylsiloxane) α,ω-diol residues (C), and represented by the following formula

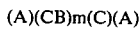

wherein these residues are linked by ether bonds, respectively.

$R_1$ in the above general formula (I) is a polymerization initiator residue of ε-caprolactone as described above, and the said polymerization initiators contain alcohol groups. For such alcohol groups, polyhydric alcohols, preferably bivalent alcohols are used, and tervalent to sixvalent alcohols may be used also. Concretely, aliphatic, aromatic and alicyclic polyhydric alcohols are included.

The following compounds may be included as the aliphatic polyhydric alcohols; alkylene glycols such as ethylene glycol, 1,2-propylene glycol, 1,3-propylene glycol, 1,3-butanediol, 1,4-butanediol, 2,3-butylene glycol, pentamethylene glycol and hexamethylene glycol, as the aromatic polyhydric alcohols; diols which contain aromatic nucleus such as isophthalyl alcohol, terephthalyl alcohol, β',β-bishydroxyethyl terephthalate and β',β-bishydroxyethyl isophthalate, as alicyclic polyhydric alcohols; alicyclic compounds such as cyclohexane-1,4-diol and cyclohexane-1,4-dimethanol, furthermore, polymers which contain oligomers of polyether diol, polyether diol, polyacetal diol, polyesteramide diol, polyesterether diol and polyhydrocarbon diol, concretely, oligomers of polyethylene glycols such as diethylene glycol and triethylene glycol, polypropylene glycol, polytetramethylene glycol, polyethylene adipate diol, polypropylene adipate diol, polybutylene adipate diol, polyethylene sebacate diol, polyethylene propylene diol, polyethylene butylene diol, polyethylene diol, polypropylene diol, etc. The following compounds may be also included as tervalent alcohols; trimethylol propane, glycerol, etc., as tetravalent alcohols; pentaerythritol diglycerol, as sixvalent alcohols; dipenta erythritol, sorbitol, etc.

In addition, the compounds may contain amine groups, etc.

$R_2$ in the general formula (I) are polymerization initiator residues of ε-caprolactone as described previously, if the polymerization initiator has an active hydrogen and can produce a terminal OH group, any compound may be included as the said initiator, concretely, monoalcohols may be included.

As the monoalcohols, aliphatic, aromatic and alicyclic alcohols are contained. As the aliphatic alcohols, alkyl alcohols such as methyl alcohol, ethyl alcohol, propyl alcohol, isopropyl alcohol, butyl alcohol, isobutyl alcohol and octyl alcohol, and monoalcohols except alkyl alcohols such as methoxy butanol, are included. As the aromatic alcohols, benzyl alcohol, etc., are cited. As the alicyclic alcohols, cyclohexinyl methanol, etc.

In addition, the compounds may contain amine groups, etc.

Furthermore, for $n_1$, $n_2$, $n_3$, $n_4$ and m which are unit numbers of structure in the said general formula, preferably, $n_1$ is 20~200, $n_2+n_3$ is 20~400, $n_4$ is 60~800 and m is 0~20, respectively.

Compounds of the present invention are new compounds which are undisclosed in literatures and can be prepared by the following chemical reaction.

For example, a polycaprolactone alone represented by general formula

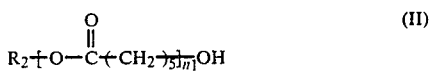
(II)

wherein $R_2$ and $n_1$ have the same meanings described above, or a mixture of the range of 1 to 10~2 to 1 of mole ratio of the compound (II) and a polycaprolactone represented by the following general formula

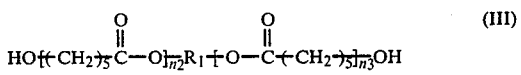
(III)

wherein $R_1$, $n_2$ and $n_3$ have the same meanings described above, is reacted with stoichiometrically excess α,ω-bis(dimethyl amino)octamethyl tetrasiloxane to produce a derivative of the compound (II), namely a compound (IV) represented by the following general formula

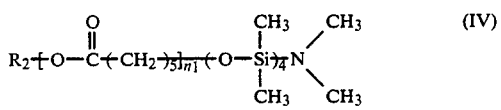
(IV)

or a derivative of the compound (III), namely a compound (V) represented by the following general formula

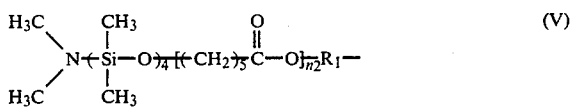
(V)

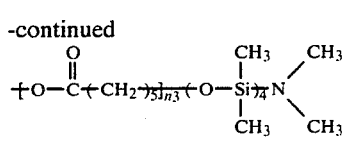

Then, the obtained compound (IV) alone or a mixture of the compounds (IV) and (V) is reacted with much the same mole of poly(dimethylsiloxane) α,ω-diol represented by the following general formula

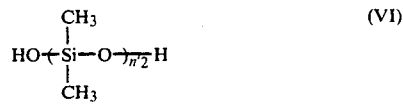
(VI)

wherein $n'_4$ is a number of structure units and corresponds to $n_4-8$, to produce the compounds of the present invention.

In general, the above reaction of the compounds (II) and (III) with α,ω-bis(dimethylamino)octamethyl tetrasiloxane advantageously proceeds to room temperature or by heating in the presence of a solvent in a dehumidifying system. For the solvent, aromatic hydrocarbons such as benzene, toluene or xylene and N,N-dimethyl formamide, etc. can be used. If moisture in the reaction system decreases, it will be able to depress side reactions of polycondensation reaction and the like.

The reaction temperature which does not always keep constant in kinds of materials and solvents and other conditions is selected in the range of room temperature to 50° C.

The unreacted α,ω-bis(dimethylamino)octamethyl tetrasiloxane which is still present in the reaction system as distilled under reduced pressure together with the solvent to remove outside of the system, prior to reaction of the product with the compound (VI).

The reaction of the above reaction product (IV) alone after removal of unreacted α,ω-bis(dimethylamino)octamethyl tetrasiloxane, or a mixture of products (IV) and (V) with the compound (VI), in a similar manner as the preceding reaction, in general, proceeds advantageously by heating in the presence of a solvent in a dehumidifying system. For the solvent, in a similar manner as the preceding reaction, aromatic hydrocarbons, N,N-dimethyl amide, etc. can be used. The reaction temperature is usually selected in the range of 40°-60° C.

The solvent is allowed to evaporate slowly from the reaction mixture solution, so that the desired rubberlike compound is obtained. In this case, as unreacted polycaprolactone and polysiloxane separate into phases macroscopically, they are removed. Further, this rubberlike compound is again dissolved into a solvent, and a pure product are obtained by fractional precipitation.

The desired material isolated in this manner exhibits the property of plasticity by heating, and exhibits the property of its original rubber elastomer by cooling again to room temperature.

Upon removing the solvent from the solution, the compound of the present invention does not show macroscopic phase separation, but show characteristic absorption derived from ester bonding and siloxane bonding at near 1,700 cm$^{-1}$ and 1,100 cm$^{-1}$, respectively, as shown in the infrared spectrum of FIG. 1(c), so that the compound can be identified as a single copolymer.

The compound of the present invention is a block copolymer which has polycaprolactone chains as hard segments and polysiloxane chains as soft segments. Since the crystalline hard segments act as a physical cross linking point of the soft segments at ordinary temperature, the compound shows almost the same dynamic characteristic as that of conventional vulcanized silicone rubber.

Upon a little heating (50°–60° C.), the compound becomes its plastic state like unvulcanized liquid rubber for the sake of sharp fusion of the crystal of the hard segments. Namely, rubber and liquid states are obtained reversibly by different temperatures.

DETAILED DESCRIPTION OF THE PREFERRED EMBODIMENTS

The following non-limiting examples illustrate the embodiments of the present invention.

EXAMPLE 1

0.4 g of polycaprolactone having a hydroxyl group at one end of the chain (molecular weight: 5,000, $n_1=44$) which is obtained by ring opening polymerization at 150°–200° C. for a few hours after adding n-butanol as a polymerization initiator into ε-caprolactone monomer, and 0.64 g of polycaprolactone having hydroxyl groups at the both ends of the chain (molecular weight: 4,000, $n_2+n_3=35$) which is obtained by ring opening polymerization in the same manner described above after adding ethylene glycol into ε-caprolactone monomer, were dissolved in 50 ml of benzene. This solution was successively added to great excess α,ω-bis(dimethylamino)octamethyl tetrasiloxane over three hours under dry nitrogen atmosphere with stirring. The solution was then heated to 50°–55° C. and continuously stirred further for three hours.

Unreacted α,ω-bis(dimethylamino)octamethyl tetrasiloxane was distilled away from the reaction mixture under reduced pressure (below 0.2 mmHg) over 5–6 hours. After 50 ml of benzene was added to the solid residue to dissolve, 8 g of poly(dimethylsiloxane) α,ω-diol(molecular weight: 40,000, $n'_4=540$) was added to the obtained solution and stirred at temperature below 45° C. for 5 hours and then at 60° C. for 6 hours.

Benzene was allowed to evaporate slowly from the obtained reaction mixture over 48 hours. Further, benzene was removed under reduced pressure for 24 hours and a rubber-like multiblock copolymer corresponding to m=3 was obtained. In this case, as unreacted polycaprolactone and poly(dimethylsiloxane) were slightly separated into phases, its solid polycaprolactone phase and adhesive liquid poly(dimethylsiloxane) phase were removed. After the rubber phase was again dissolved in benzene, the desired rubber phase was isolated and purified by fractional precipitation.

Figure 1A:
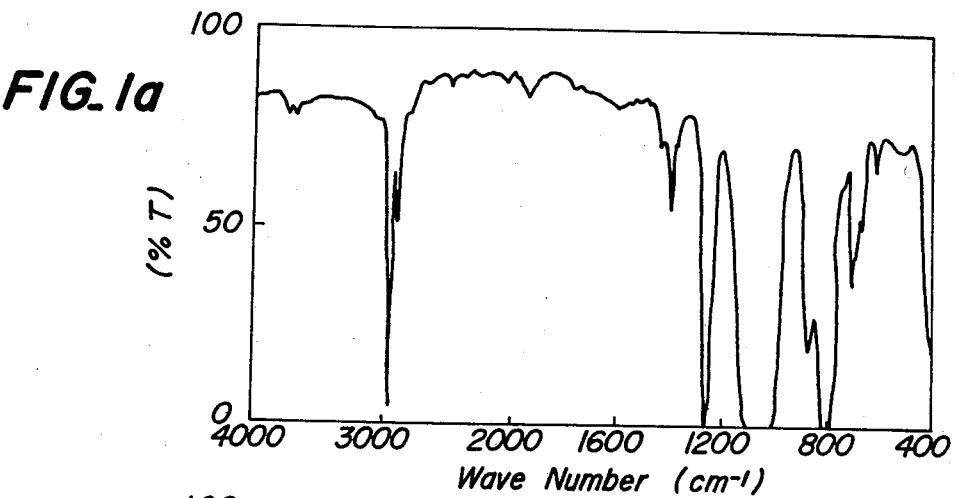
FIG. 1(a) is a diagram of an infrared spectrum of polysiloxane which is soft segments of a block copolymer.
Figure 1B:
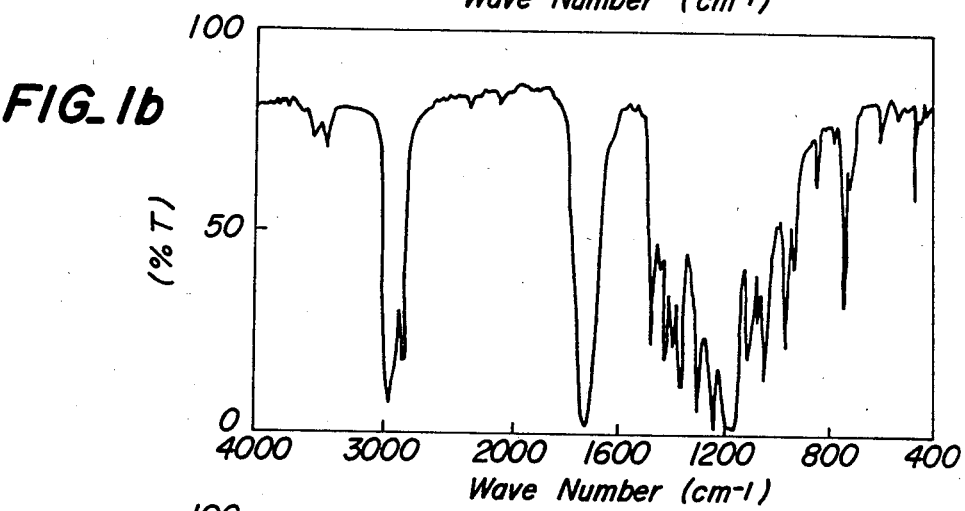
FIG. 1(b) is a diagram of an infrared spectrum of polycaprolactone which is hard segments of a block copolymer.
Figure 1C:
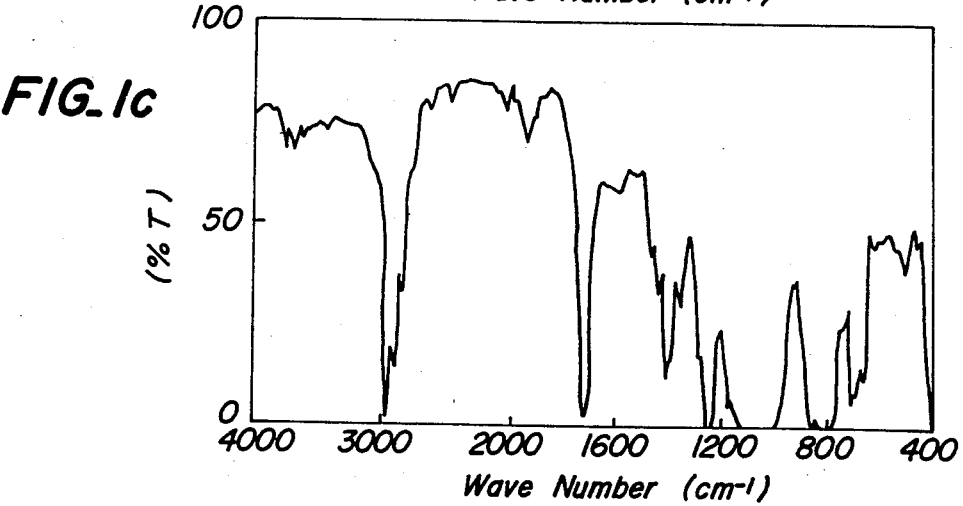
FIG. 1(c) is a diagram of an infrared spectrum of the compound obtained by example 1.

The infrared spectrum of polysiloxane which is the soft segment of the block copolymer shows in FIG. 1(a), the infrared spectrum of polycaprolactone which is the hard segment of the block copolymer in FIG. 1(b), and the infrared spectrum of the obtained rubber phase in FIG. 1(c).

Figure 2:
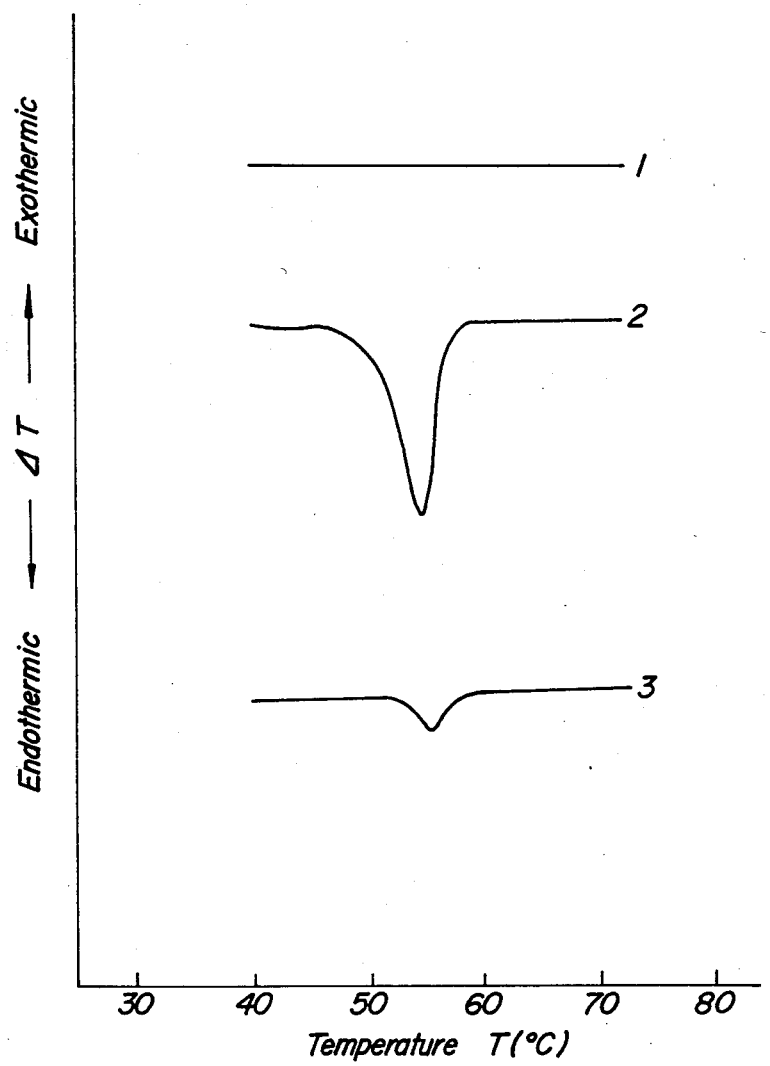
FIG. 2 is a diagram which shows the result of differential thermal analysis of the compound obtained by example 1, poly(dimethylsiloxane) and polycaprolactone.

The dynamic elastic modulus of this rubber phase is 0.3–0.5 MPa at the frequency in the range of 20–70 Hz at room temperature, as shown in the result of differential thermal analysis exhibited by FIG. 2, the rubber phase is melted on the basis of melting of the hard segment at temperature near to 55° C. Moreover, FIG. 2 shows thermal characteristics in the result of differential thermal analysis of poly(dimethylsiloxane) (line 1), polycaprolactone (line 2) and the compound of example 1 (line 3). Further, the flow properties of the melt are different by temperatures, so that the rubber phase was a fluid having a yield point of about $10^3$ Pa at 80° C. and an apparent viscosity of $6\times10^2$ Pa.S and below at a shear rate of 2 $sec^1$ and over.

EXAMPLE 2

Using 2.5 g of polycaprolactone (molecular weight: 5,000, $n_1=44$) which has an n-butanol residue of the polymerization initiator at the one end and its hydroxyl group at the other end and 8 g of poly(dimethylsiloxane) α,ω-diol (molecular weight: 40,000, $n'_4=540$), a copolymer in the same procedure as in Example 1 was synthesized, and the obtained rubber phase was isolated to purify.

Namely, in this example, a teleblock copolymer (m=0) was synthesized by using the monofunctional polycaprolactone as the hard segment of the block copolymer.

The dynamic elastic modulus of the obtained rubber phase was about 0.2–0.5 MPa at the frequency in the range of 20–70 Hz at room temperature as well as the multiblock copolymer of Example 1. The melting temperature was also about 55° C. as well as the copolymer of Example 1, but the apparent viscosity at the shear rate of 2 $sec^{-1}$ and over was $10^2$ Pa.S and below at 80° C.

As mentioned above, the low modulus thermoplastic elastomers of the present invention are block copolymers comprised of polycaprolactone chains as hard segments and polysiloxane chains as soft segments. As conventional silicones of vulcanized type can not return to the shapable state if once the compounds have vulcanized, these cannot use repeatedly as materials. Contrarily, the compounds of the present invention can use repeatedly, especially, these are effective against reduction of expenses as dental impression materials and mold materials for general uses, and these can be applied in a wide range of uses as various sealing materials and toy materials made of rubber. Further, in handling them, differing from the rubber of vulcanized type, it is easy to handle because there is no necessity for considering conditions of chemical reaction such as mixing of reaction components. Further, as the compounds of the present invention are widely changeable their chain length of hard segments, soft segments and the combination of both segments, the effect of the present invention is to provide the compounds having a necessary dynamic property and a physico-chemical property according to the object of use.

What is claimed is:

1. A polyester-polysiloxane block copolymer represented by the following general formula $$R_2 + O - \overset{O}{\underset{\|}{C}} + CH_2 \overset{}{)_5}]_{\overline{n_1}} O + \overset{CH_3}{\underset{\underset{CH_3}{|}}{\overset{|}{Si}}} - O \overset{}{)_{\overline{n_4}}} + CH_2 \overset{}{)_5} \overset{O}{\underset{\|}{C}} - O \overset{}{]_{\overline{n_2}}}$$

$$- R_1 + O - \overset{O}{\underset{\|}{C}} + CH_2 \overset{}{)_5}]_{\overline{n_3}} O + \overset{CH_3}{\underset{\underset{CH_3}{|}}{\overset{|}{SiO}}} \overset{}{)_{\overline{n_4}}} + CH_2 \overset{}{)_5} \overset{O}{\underset{\|}{C}} - O \overset{}{]_{\overline{n_1}}} - R_2 \bigg]_m$$

(I)

wherein $R_1$ is a polymerization initiator residue of ε-caprolactone having two or more terminal OH, $R_2$ is a polymerization initiator residue of ε-caprolactone having a single terminal OH, $n_1$ is from about 20 to about 200, $n_2 + n_3$ is from about 20 to about 400, $n_4$ is from about 60 to about 800, and $m$ is from about 0 to about 20.

2. The block copolymer of claim 1 having a Young's modulus of up to and including about 2 MPa.

3. The block copolymer of claim 1 having a viscosity at the time of fusion of up to and including about $10^3$ Pa.S.

4. The block copolymer of claim 1 having a sharp softening temperature of about 50° C.

5. The block copolymer of claim 1 wherein $R_1$, is a polyhydric alcohol.

6. The block copolymer of claim 5 wherein the polyhydric alcohol is selected from the group consisting of ethylene glycol, 1,2-propylene glycol, 1,3-propylene glycol, 1,3-butanediol, 1,4-butanediol, 2,3-butylene glycol, pentamethylene glycol, hexamethylene glycol, isophthalyl alcohol, terephthalyl alcohol, β',β-bishydroxyethyl terephthalate, β',β-bishydroxyethyl isophthalate, cyclohexane-1,4-diol, cyclohexane-1,4-dimethanol, diethylene glycol, triethylene glycol, polypropylene glycol, polytetramethylene glycol, polyethylene adipate diol, polypropylene adipate diol, polybutylene adipate diol, polyethylene sebacate diol, polyethylene propylene diol, polyethylene butylene diol, polyethylene diol, polypropylene diol, trimethylol propane, glycerol, pentaerylthritol diglycerol, dipenta erythritol, and sorbitol.

7. The block copolymer of claim 1 wherein $R_2$ is a monoalcohol.

* * * * *